(12) United States Patent
Shigematsu et al.

(10) Patent No.: US 8,671,943 B2
(45) Date of Patent: Mar. 18, 2014

(54) BREATHING APPARATUS

(75) Inventors: Nobuo Shigematsu, Tokyo (JP);
Hiroyuki Ide, Tokyo (JP)

(73) Assignee: Shigematsu Works Co., Ltd., Tokyo (JP)

( * ) Notice: Subject to any disclaimer, the term of this patent is extended or adjusted under 35 U.S.C. 154(b) by 361 days.

(21) Appl. No.: 12/746,476

(22) PCT Filed: Sep. 17, 2008

(86) PCT No.: PCT/JP2008/066755
§ 371 (c)(1),
(2), (4) Date: Aug. 26, 2010

(87) PCT Pub. No.: WO2009/072337
PCT Pub. Date: Jun. 11, 2009

(65) Prior Publication Data
US 2010/0313892 A1 Dec. 16, 2010

(30) Foreign Application Priority Data

Dec. 7, 2007 (JP) ................................. 2007-316671

(51) Int. Cl.
*A62B 18/02* (2006.01)
*F16K 31/02* (2006.01)
*A62B 7/00* (2006.01)

(52) U.S. Cl.
USPC ............. 128/205.25; 128/206.21; 128/204.23

(58) Field of Classification Search
USPC ............. 128/205.25, 204.16, 204.18, 204.21, 128/204.23, 206.21, 201.28, 205.24, 128/207.12; 600/529
See application file for complete search history.

(56) References Cited

U.S. PATENT DOCUMENTS

| | | | | | |
|---|---|---|---|---|---|
| 4,886,056 | A | * | 12/1989 | Simpson | 128/201.25 |
| 5,069,221 | A | * | 12/1991 | Smith et al. | 600/534 |
| 5,541,538 | A | * | 7/1996 | Bacrania et al. | 327/77 |
| 7,111,625 | B2 | * | 9/2006 | Jackson | 128/205.24 |
| 2004/0244797 | A1 | | 12/2004 | Jackson | |
| 2007/0163588 | A1 | * | 7/2007 | Hebrank et al. | 128/204.18 |

FOREIGN PATENT DOCUMENTS

| | | |
|---|---|---|
| JP | 60-68869 A | 4/1985 |
| JP | 2-74267 A | 3/1990 |
| JP | 7-172120 A | 7/1995 |
| JP | 10-028744 | 2/1998 |

(Continued)

OTHER PUBLICATIONS

Office Action issued in co-pending Japanese patent application 2007-316671 dated May 9, 2012 (no translation available; submitted for certification).

(Continued)

*Primary Examiner* — Jackie Ho
*Assistant Examiner* — Ned T Heffner
(74) *Attorney, Agent, or Firm* — Griffin & Szipl, P.C.

(57) ABSTRACT

A breathing apparatus including a face piece for covering the whole face or part of the face, an inhale valve and an exhale valve provided on the face piece, a motor fan for supplying external air into the face piece through the inhale valve, a filter for cleaning the external air sucked into the motor fan, a breath monitoring apparatus provided on the face piece and not comprising the inhale valve and the exhale valve, and a controller for controlling the operation of the motor fan synchronously with the breath based on the detection signal from the breath monitoring apparatus.

7 Claims, 3 Drawing Sheets

(56) References Cited

FOREIGN PATENT DOCUMENTS

| JP | 2001-324399 A | 11/2001 |
| JP | 2003-737 A | 1/2003 |
| JP | 2003-10349 A | 1/2003 |
| JP | 3726886 | 10/2005 |
| JP | 3726886 B2 | 10/2005 |

OTHER PUBLICATIONS

International Search Report issued in corresponding application PCT/JP2008/066755, completed Dec. 15, 2008, mailed Dec. 22, 2008.

Random House Webster'S College Disctionary 516 (1991).

* cited by examiner

BREATHING APPARATUS

This is a National Phase Application in the United States of International Patent Application No. PCT/JP2008/066755 filed Sep. 17, 2008, which claims priority on Japanese Patent Application No. 2007-316671, filed Dec. 7, 2007. The entire disclosures of the above patent applications are hereby incorporated by reference.

TECHNICAL FIELD OF THE INVENTION

The present invention relates to a breathing apparatus.

BACKGROUND OF THE INVENTION

Including Art

Patent Document No. 1 teaches a breathing apparatus comprising a face piece for covering the whole face or part of the face, an inhale valve and an exhale valve provided on the face piece, a motor fan for supplying external air into the face piece through the inhale valve, a filter for cleaning the external air sucked into the motor fan, a breath monitoring apparatus comprising the exhale valve and a photo sensor for detecting the position of the exhale valve, and a controller for controlling the operation of the motor fan synchronously with the breath based on the detection signal from the breath monitoring apparatus.
Patent Document No. 1: Japanese Patent No. 3726886

Problem to be solved

The breathing apparatus of Patent Document No. 1 has a problem in that the photo sensor is located in an exhale passage, so that micro particulates of dust, water, etc. contaminating the exhaled air are liable to adhere to the photo sensor to foul it, thereby causing deterioration with age of the accuracy of the breath monitoring. The present invention is directed to solving the aforementioned problem. An object of the present invention is to provide a breathing apparatus comprising a face piece for covering the whole face or part of the face, an inhale valve and an exhale valve provided on the face piece, a motor fan for supplying external air into the face piece through the inhale valve, a filter for cleaning the external air sucked into the motor fan, a breath monitoring apparatus, and a controller for controlling the operation of the motor fan synchronously with the breath based on the detection signal from the breath monitoring apparatus, wherein deterioration with age of the accuracy of the breath monitoring occurs less readily than in the breathing apparatus of Patent Document No. 1.

SUMMARY OF THE INVENTION

Means for Achieving the Object

In accordance with the present invention, there is provided a breathing apparatus comprising a face piece for covering the whole face or part of the face, an inhale valve and an exhale valve provided on the face piece, a motor fan for supplying external air into the face piece through the inhale valve, a filter for cleaning the external air sucked into the motor fan, a breath monitoring apparatus provided on the face piece and not comprising the inhale valve or the exhale valve, and a controller for controlling the operation of the motor fan synchronously with the breath based on the detection signal from the breath monitoring apparatus. In the breathing apparatus in accordance with the present invention, a sensor constituting a part of the breath monitoring apparatus need not be located in an inhale passage or an exhale passage because the breath monitoring apparatus does not comprise the inhale valve or the exhale valve. Therefore, micro particulates of dust, water, etc. contaminating the inhaled air or the exhaled air do not readily adhere to the sensor to foul it. Therefore, deterioration with age of the accuracy of the breath monitoring occurs less readily than in the breathing apparatus of Patent Document No. 1.

In accordance with a preferred embodiment of the present invention, the controller starts the motor fan based on a detection signal from the breath monitoring apparatus when the breath monitoring apparatus detects the breath, thereafter controls the operation of the motor fan synchronously with the breath based on the detection signal from the breath monitoring apparatus, and stops the motor fan when the breath monitoring apparatus does not detect the breath for a predetermined time. A breathing apparatus equipped with a motor fan generally comprises an ON/OFF switch of the motor fan. Therefore, the user manually operates the ON/OFF switch of the motor fan when he or she uses the breathing apparatus. It is troublesome for the user to operate the ON/OFF switch of the motor fan after he or she had puts on the breathing apparatus, thereby diminishing the convenience of the breathing apparatus. However, in accordance with the structure of the aforementioned preferred embodiment, the user need not manually operate an ON/OFF switch of the motor fan after he or she puts on the breathing apparatus because the motor fan automatically starts when he or she puts on the breathing apparatus to start breathing and automatically stops when he or she takes off the breathing apparatus. As a result, the convenience of the breathing apparatus increases.

In accordance with a preferred embodiment of the present invention, the breath monitoring apparatus comprises a diaphragm covering an opening formed in the face piece, a magnet provided on the diaphragm and a Hall element disposed opposite the magnet and provided on the face piece. Internal pressure of the face piece changes according to the state of the breath, the diaphragm receives the internal pressure to displace, the distance between the magnet and the Hall element changes, and magnetic flux density detected by the Hall element changes. Therefore, the controller can recognize the state of the breath based on the result of the detection by the Hall element. The Hall element is a magnetometric sensor. Therefore, the accuracy of detection by the Hall element is less readily decreased than that of a photo sensor even if particulates of dust, water, etc. contaminating the internal air of the face piece adhere to the Hall element. Therefore, deterioration with age of the accuracy of the breath monitoring occurs less readily than in the breathing apparatus of Patent Document No. 1.

In accordance with a preferred embodiment of the present invention, the diaphragm is a membrane body comprising a circular disk portion $7a_1$ and an annular portion constituted by folding the periphery $7a_2$ of the circular disk portion radially inward, and the inner periphery $7a_3$ of the annular portion is fixed to the outside surface of a portion of an annular drum connected to the periphery of the opening formed in the face piece projecting out of the face piece. In the diaphragm, whose periphery is folded radially inward, difference in displacement of the circular disk portion caused by the change of the internal pressure of the face piece, i.e. difference between the displacement of the circular disk portion in inhaling condition and that in exhaling condition is large because the folded portion can open and close. Therefore, the breathing apparatus in accordance with the present invention can accurately monitor the breath and reliably operate the motor fan synchronously with the breath.

In accordance with a preferred embodiment of the present invention, the breathing apparatus further comprises an alarm, the breath monitoring apparatus is an apparatus for monitoring the internal pressure of the face piece, and the controller starts the alarm when the apparatus for monitoring the internal pressure of the face piece detects negative pressure. Airflow resistance of the filter increases with age due to accumulation of dust to decrease with age the flow rate of the motor fan. Heretofore, the flow rate of the motor fan was measured with a dedicated device for measuring flow rate before the breathing apparatus was put on the user and the filter was changed when the flow rate was insufficient. However, flow rate measurement before putting on the breathing apparatus is troublesome for the user. Airflow resistance of the filter increases with age due to accumulation of dust to decrease with age the flow rate of the motor fan. Even if the flow rate of the motor fan decreases, breathing trouble is prevented if the internal pressure of the face piece is kept positive during inhale. On the other hand, if the internal pressure of the face piece becomes negative during inhale, breathing trouble is experienced and non-filtered external air is liable to flow into the face piece through the space between the periphery of the face piece and the face of the user. Therefore, it is desirable to inform the user of the breathing apparatus of insufficient flow rate of the motor fan so as to prompt the user to replace the filter when the decrease of the flow rate reaches a level causing negative internal pressure of the face piece. When the breath monitoring apparatus is structured as an apparatus for monitoring the internal pressure of the face piece to activate the alarm when it detects negative internal pressure of the face piece, the user of the breathing apparatus can easily perceive the flow rate deficiency without carrying out the troublesome flow measurement before putting on the breathing apparatus.

In accordance with a preferred embodiment of the present invention, the apparatus for monitoring the internal pressure of the face piece comprises a diaphragm covering an opening formed in the face piece, a magnet provide on the diaphragm and a Hall element disposed opposite the magnet and provided on the face piece, the diaphragm is a membrane body comprising a circular disk portion and an annular portion constituted by folding the periphery of the circular disk portion radially inward, the inner periphery of the annular portion is fixed to the outside surface of a portion of an annular drum connected to the periphery of the opening formed in the face piece projecting out of the face piece, the circular disk portion becomes flat to abut the end of the portion of the annular drum projecting out of the face piece at the radial middle when the internal pressure of the face piece balances with the external pressure of the face piece, and the magnet is provided on the center of the circular disk portion. In the aforementioned breathing apparatus, the diaphragm swells out of the face piece when the internal pressure of the face piece is positive to separate from the end of the portion of the annular drum projecting out of the face piece at the circular disk potion. The circular disk portion becomes flat when the internal pressure of the face piece is equal to the atmospheric pressure to abut the end of the portion of the annular drum projecting out of the face piece at the radial middle. The circular disk portion abuts the end of the portion of the annular drum projecting out of the face piece at the radial middle when the internal pressure of the face piece is negative to subside into the internal space of the annular drum at the center. The Hall element detects change of magnetic flux density of the magnet to detect the subsidence of the center of the circular disk portion of the diaphragm into the internal space of the annular drum. The controller recognizes the negative internal pressure of the face piece based on the detection signal from the Hall element to start the alarm. In a case where an external impact force or an external vibration force is applied to the diaphragm to push it against the annular drum when the positive internal pressure of the face piece decreases due to inhale, the aforementioned force is applied not only to a first portion of the diaphragm located radially inside the portion abutting the annular drum but also to a second portion of the diaphragm located radially outside the portion abutting the annular drum. The force applied to the first portion makes it subside into the internal space of the annular drum. The force applied to the second portion raises the first portion from the internal space of the annular drum because the diaphragm is supported by the annular drum at the portion between the first portion and the second portion. As a result, the subsidence of the first portion into the internal space of the annular drum is suppressed. Therefore, in the breathing apparatus in accordance with the present invention, erroneous operation of the alarm due to an impact force or a vibration force is inhibited. When the internal pressure of the face piece becomes negative, the displacement of the diaphragm becomes maximum at the center. Therefore, the negative pressure in the face piece can be reliably detected by the Hall element detecting the deflection of the center of the diaphragm.

Effect of the Invention

In accordance with the present invention, there is provided a breathing apparatus comprising a face piece for covering the whole face or part of the face, an inhale valve and an exhale valve provided on the face piece, a motor fan for supplying external air into the face piece through the inhale valve, a filter for cleaning the external air sucked into the motor fan, a breath monitoring apparatus, and a controller for controlling the operation of the motor fan synchronously with the breath based on the detection signal from the breath monitoring apparatus, wherein deterioration with age of the accuracy of the breath monitoring occurs less readily than in the breathing apparatus of Patent Document No. 1.

DETAILED DESCRIPTION OF THE INVENTION

Best Mode for Carrying Out the Invention

Figure 1:
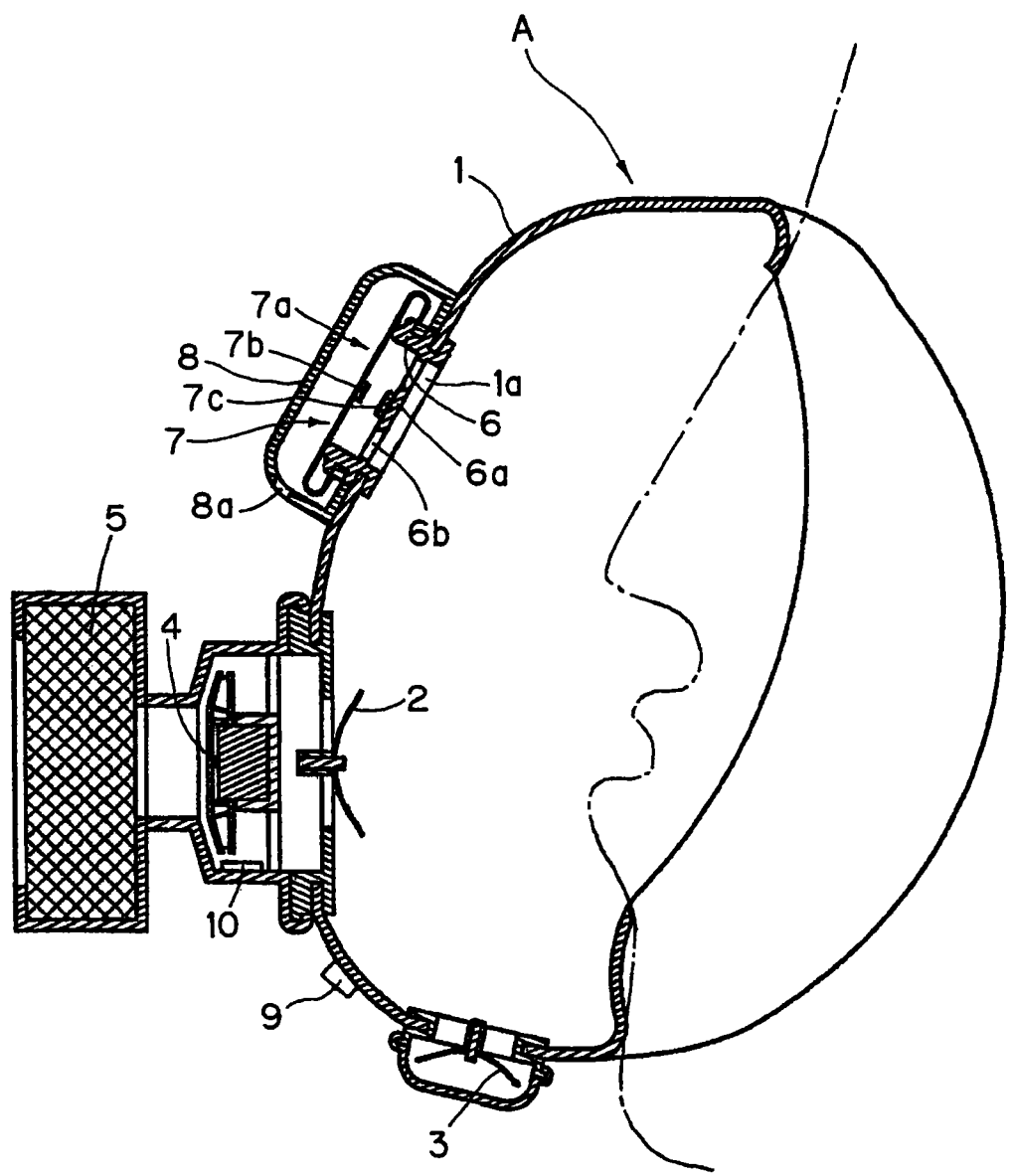
FIG. 1 is a sectional view of a breathing apparatus in accordance with a preferred embodiment of the present invention.
Figure 2:
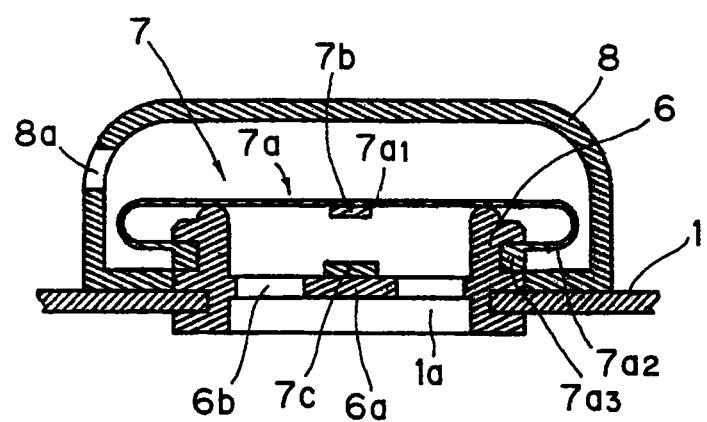
FIG. 2 is a sectional view of a breath monitoring apparatus provided on the breathing apparatus in accordance with a preferred embodiment of the present invention when the breathing apparatus is not in use.

A breathing apparatus in accordance with a preferred embodiment of the present invention will be described. As shown in FIG. 1, a breathing apparatus A comprises a bowl-shaped face piece 1 for covering the whole face or part of the face indicated by a chain line in the figure, an inhale valve 2 and an exhale valve 3 which are formed as reed valves and provided on the face piece 1, a motor fan 4 located outside the inhale valve 2 to supply external air into the face piece 1 through the inhale valve 2, and a filter 5 located outside the motor fan 4 to clean the external air sucked into the motor fan 4. As shown in FIGS. 1 and 2, an opening 1a is formed in the face piece 1 in addition to an inhale opening opened and closed by the inhale valve 2 and an exhale opening opened and closed by the exhale valve 3. An annular drum 6 fits in the opening 1a and is fixed to the periphery of the opening 1a. The annular drum 6 is provided with a partition 6a at its longitudinal middle. The partition 6a is provided with a plurality of holes 6b at the outer periphery. The holes 6b are circumferentially distanced from each other.

The breathing apparatus A comprises a breath monitoring apparatus 7. The breath monitoring apparatus 7 comprises a diaphragm 7a. The diaphragm 7a is a flexible membrane body comprising a circular disk portion $7a_1$ and an annular portion $7a_2$ constituted by folding the periphery of the circular disk portion $7a_1$ radially inward. Inner periphery of the annular portion $7a_2$ forms a thick portion $7a_3$. The thick portion $7a_3$ fits in and is fixed to a circumferential groove formed on the outside surface of a portion of the annular drum 6 projecting out of the face piece 1. The diaphragm 7a covers one end of the annular drum 6 projecting out of the face piece 1 to cover the opening 1a of the face peace 1. The breath monitoring apparatus 7 comprises a magnet 7b provided on the center of the circular disk portion $7a_1$ and a Hall element 7c located opposite the magnet 7b and provided on the partition 6a of the annular drum 6. Therefore, the Hall element 7c is provided on the face piece 1 through the annular drum 6.

A cover 8 is provided on the outside surface of the face piece 1 to cover the breath monitoring apparatus 7. The cover 8 is provided with an air whole 8a communicating with the external environment. An alarm 9 is provided on the face piece 1. A controller 10 is disposed close to the motor fan 4 to control the operations of the motor fan 4 and the alarm 9 based on the output signal of the Hall element 7c. A battery not shown in the Figures is detachably provided on the face piece 1 to supply the controller 10 with electric power. When the battery is attached to the face piece 1, the controller 10 is continuously supplied with electric power.

Figure 3:
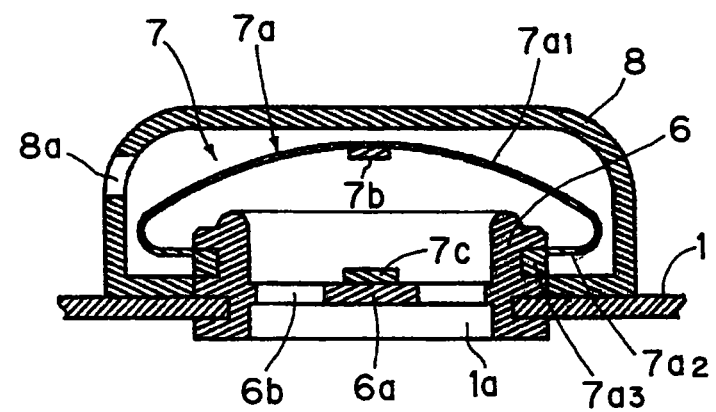
FIG. 3 is a sectional view of a breath monitoring apparatus provided on the breathing apparatus in accordance with a preferred embodiment of the present invention when the breathing apparatus is used in exhaling condition.
Figure 4:
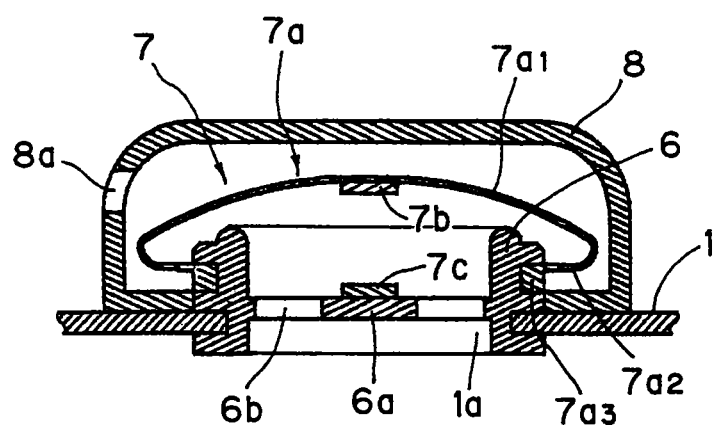
FIG. 4 is a sectional view of a breath monitoring apparatus provided on the breathing apparatus in accordance with a preferred embodiment of the present invention when the breathing apparatus is used in inhaling condition.
Figure 5:
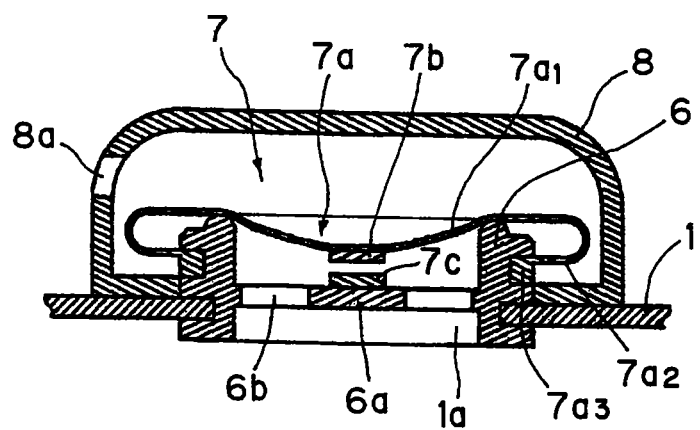
FIG. 5 is a sectional view of a breath monitoring apparatus provided on the breathing apparatus in accordance with a preferred embodiment of the present invention when the breathing apparatus is used in inhaling condition, with the life of the filter already expired.

Operation of the breathing apparatus A will be described. When the breathing apparatus A is not in use, the internal pressure (gage pressure) of the face piece 1 is zero, so that the internal pressure and the external pressure applied to the diaphragm 7a balance with each other. In the following description, the internal pressure of the face piece 1 is gage pressure. As shown in FIG. 2, the diaphragm 7a is in the initial condition, wherein the circular disk portion $7a_1$ becomes flat to abut the end of the portion of the annular drum 6 projecting out of the face piece 1 at the radial middle. When the diaphragm 7a is in the initial condition, the distance between the magnet 7b and the Hall element 7c becomes the initial value, and the magnetic flux density detected by the Hall element 7c also becomes the initial value. When the internal pressure of the face piece 1 is positive, the diaphragm 7a swells out of the face piece 1 as shown in FIGS. 3 and 4 and the circular disk portion $7a_1$ separates from the end of the portion of the annular drum 6 projecting out of the face piece 1. When the internal pressure of the face piece 1 is negative, the diaphragm 7a subsides toward the internal space of the face piece 1 as shown in FIG. 5, the circular disk portion $7a_1$ abuts the end of the portion of the annular drum 6 projecting out of the face piece 1 at the radial middle, and the center of the circular disk portion $7a_1$ subsides into the internal space of the annular drum 6.

When the breathing apparatus A is used, the face piece 1 is put on the head of the user so as to cover a part of the face of the user including the nose and mouth indicated by the chain line in FIG. 1 or the whole face of the user. The annular periphery of the face piece 1 tightly abuts the face of the user to prevent the external air from flowing into the face piece through the abutting portion between the annular periphery of the face piece and the face of the user. The battery is provided on the face piece 1 and the controller 10 operates. Corresponding to the exhale and inhale of the user, the internal pressure of the face piece 1 increases and decreases, pressure difference is generated between the internal pressure and the external pressure applied to the diaphragm 7a, the diaphragm 7a displaces from the initial condition, and the distance between the magnet 7b and the Hall element 7c changes from the initial value. The Hall element 7c detects the change of the magnetic flux density from the initial value caused by the aforementioned change of the distance to send a detection signal to the controller 10. The controller 10 recognizes that the breathing apparatus A was put on the head of the user when the change of the magnetic flux density from the initial value received from the Hall element 7c exceeds a predetermined level to start the motor fan 4. The controller 10 controls the rotation speed of the motor fan 4 based on the detection signal from the Hall element 7c so that the internal pressure of face piece 1 becomes positive and the diaphragm 7a lies more outside the face piece 1 after displacement than in the initial condition.

During exhale, the internal pressure of the face piece 1 increases, the displacement of the diaphragm 7a out of the face piece 1 increases as shown in FIG. 3, the distance between the magnet 7b and the Hall element 7c increases, and the magnetic flux density detected by the Hall element 7c decreases. When the increment of the aforementioned distance from the initial value exceeds a predetermined level and the decrement of the magnetic flux density detected by the Hall element 7c from the initial value exceeds a predetermined level, the controller recognizes that the breathing is in exhaling condition to decrease the rotation speed of the motor fan 4 or stop the motor fan 4. As a result, electric power consumption is saved, discharge of the battery is suppressed, and clogging of the filter 5 is suppressed. During exhale, the inhale valve 2 closes and the exhale valve 3 opens. The exhaled air is exhausted into the external environment through the exhale valve 3.

During inhale, the internal pressure of the face piece 1 decreases, the displacement of the diaphragm 7a out of the face piece 1 decreases as shown in FIG. 4, the distance between the magnet 7b and the Hall element 7c decreases, and the magnetic flux density detected by the Hall element 7c increases. When the increment of the aforementioned distance from the initial value becomes equal to or less than the predetermined level and the decrement of the magnetic flux density detected by the Hall element 7c from the initial value becomes equal to or less than the predetermined level, the controller recognizes that the breathing is in inhaling condition to increase the rotation speed of the motor fan 4. During inhale, the inhale valve 2 opens and the exhale valve 3 closes.

External air is passed through the filter 5 to be freed of dust, sucked into the motor fan 4, and passed into the face piece 1 through the inhale valve 2. When the rotation speed of the motor fan 4 increases, flow rate of the air introduced into the face piece 1 increases, and the internal pressure of the face piece 1 is kept positive. Thus, the breathing of the user of the breathing apparatus becomes easy.

Airflow resistance of the filter 5 increases with age due to accumulation of dust. As a result, the internal pressure of the face piece 1 during inhale decreases with age even if the motor fan 4 is operated. Finally, the internal pressure of the face piece 1 becomes negative, the diaphragm 7a subsides toward the internal space of the face piece 1 as shown in FIG. 5, the circular disk portion $7a_1$ abuts the end of the portion of the annular drum 6 projecting out of the face piece 1 at the radial middle, and the center of the circular disk portion $7a_1$ subsides into the internal space of the annular drum 6. The distance between the magnet 7b and the Hall element 7c becomes less than the initial value, and the magnetic flux density of the magnet 7b detected by the Hall element 7c increases beyond the initial value. When the magnetic flux density of the magnet 7b detected by the Hall element 7c increases beyond the initial value, the controller 10 recognizes that the life of the filter 5 has expired due to clogging and start the alarm 9, thereby prompting the user of the breathing apparatus A to change the filter 5. When the filter 5 is changed, the internal pressure of the face piece 1 comes to be controlled again to become positive, and the function of the breathing apparatus A is restored.

When the breathing apparatus A is removed from the head of the user, the internal pressure and the external pressure applied to the diaphragm 7a balance with each other, the diaphragm 7a returns to the initial condition, the distance between the magnet 7b and the Hall element 7c returns to the initial value, and the magnetic flux density of the magnet 7b detected by the Hall element 7c returns to the initial value. When the magnetic flux density of the magnet 7b is kept at the initial value for a predetermined time, the controller 10 recognizes that the breathing apparatus A was removed from the head of the user to stop the motor fan 4.

In the breathing apparatus A, the Hall element 7c constituting a part of the breath monitoring apparatus 7 need not be located in an inhale passage or an exhale passage because the breath monitoring apparatus 7 does not comprise the inhale valve 2 or the exhale valve 3. Therefore, particulates of dust, water, etc. contaminating the inhaled air or the exhaled air do not readily adhere to the Hall element 7c or foul it. Therefore, deterioration with age of the accuracy of the breath monitoring apparatus 7 occurs less readily than in the breathing apparatus of Patent Document No. 1.

In the breathing apparatus A, the user need not manually operate an ON/OFF switch of the motor fan 4 after he or she put on the breathing apparatus A because the motor fan 4 automatically starts when he or she puts on the breathing apparatus A to start breathing and automatically stops when he or she takes off the breathing apparatus. As a result, the convenience of the breathing apparatus A increases.

The Hall element 7c is a magnetometric sensor. Therefore, the accuracy of detection of the Hall element 7c is less readily decreased than that in a photo sensor even if particulates of dust, water, etc contaminating the internal air of the face piece 1 adhere to the Hall element 7c. Therefore, deterioration with age of the accuracy of the breath monitoring apparatus 7 occurs less readily than in the breathing apparatus of Patent Document No. 1.

In the diaphragm 7a, wherein the periphery is folded radially inward, displacement difference of the circular disk portion $7a_1$ caused by the change of the internal pressure of the face piece 1, i.e. difference between the displacement of the circular disk portion $7a_1$ in inhaling condition and that in exhaling condition is large because the folded portion can open and close. Therefore, the breathing apparatus A can accurately monitor the breath and reliably operate the motor fan 4 synchronously with the breath.

In the breathing apparatus A, the breath monitoring apparatus 7 is structured as an apparatus for monitoring the internal pressure of the face piece to activate the alarm when it detects the negative internal pressure of the face piece. Therefore, the user of the breathing apparatus can easily perceive the deficiency of the flow rate without carrying out troublesome flow rate measurement before he or she puts on the breathing apparatus.

In a case where an external impact force or an external vibration force is applied to the diaphragm 7a to push it against the annular drum 6 when the positive internal pressure of the face piece 1 decreases due to inhalation to bring the diaphragm 7 into the initial condition, the aforementioned force is applied not only to a first portion of the diaphragm 7a located radially inside the portion abutting the end of the portion of the annular drum 6 projecting out of the face piece 1 but also to a second portion of the diaphragm 7a located radially outside the portion abutting the end of the portion of the annular drum 6 projecting out of the face piece 1. The force applied to the first portion makes it subside into the internal space of the annular drum 6. On the other hand, the force applied to the second portion raises the first portion from the internal space of the annular drum 6 because the diaphragm 7a is supported by the annular drum at the portion between the first portion and the second portion. As a result, the subsidence of the first portion into the internal space of the annular drum 6 is suppressed. Therefore, in the breathing apparatus A, erroneous operation of the alarm 9 due to impact force or vibration force is suppressed. When negative pressure occurs, the displacement of the diaphragm 7 becomes maximum at the center of the circular disk portion $7a_1$. Therefore, the negative pressure can be reliably detected by the Hall element 7c detecting the displacement of the center of the circular disk portion $7a_1$ of the diaphragm 7a.

The displacement of the diaphragm 7a can be detected by a reflector and a photo sensor comprising a light-emitter and a light-interceptor instead by the magnet 7b and the Hall element 7c.

BRIEF DESCRIPTION OF THE REFERENCE NUMERALS

A Breathing apparatus
1 Face piece
2 Inhale valve
3 Exhale valve
4 Motor fan
5 Filter
6 Annular drum
7 Breath monitoring apparatus
7a Diaphragm
7b Magnet
7c Hall element
8 Cover
9 Alarm
10 Controller Thus, in accordance with the present invention, an object is to provide a breathing apparatus comprising a face piece for covering the whole face or part of the face, an inhale valve and an exhale valve provided on the face piece, a motor fan for supplying external air into the face piece through the inhale valve, a filter for cleaning the external air sucked into the motor fan, a breath monitoring apparatus, and a controller for controlling the operation of the motor fan synchronously with the breath based on the detection signal from the breath monitoring apparatus, wherein deterioration with age of the accuracy of the breath monitoring occurs less readily than in the breathing apparatus of the prior art. In accordance with the present invention, then, a breathing apparatus comprises a face piece for covering the whole face or part of the face, an inhale valve and an exhale valve provided on the face piece, a motor fan for supplying external air into the face piece through the inhale valve, a filter for cleaning the external air sucked into the motor fan, a breath monitoring apparatus provided on the face piece and not comprising the inhale valve and the exhale valve, and a controller for controlling the operation of the motor fan synchronously with the breath based on the detection signal from the breath monitoring apparatus.

The invention claimed is:

1. A breathing apparatus comprising:
   (a) a face piece for covering a user's whole face or part of the face;
   (b) an inhale valve and an exhale valve provided on the face piece;
   (c) a motor fan supplying external air into the face piece through the inhale valve;
   (d) a filter disposed to clean the external air sucked into the motor fan;
   (e) a breath monitoring apparatus provided on the face piece and not comprising the inhale valve or the exhale valve, wherein the breath monitoring apparatus comprises
      i. a diaphragm covering an opening formed in the face piece, wherein the diaphragm is a membrane body comprising a circular disk portion and an annular portion constituted by a fold of a periphery of the circular disk portion that extends radially inward under the circular disk portion, and an inner periphery of the annular portion is fixed to an outside surface of a first portion of an annular drum connected to a periphery of the opening formed in the face piece, and the annular drum projects out of the face piece;
      ii. a magnet provided on the diaphragm; and
      iii. a Hall element disposed opposite the magnet and provided on the face piece; and
   (f) a controller connected to control operation of the motor fan synchronously with the user's breath based on a detection signal sent from the breath monitoring apparatus, wherein the controller starts the motor fan based on the detection signal sent from the breath monitoring apparatus when the breath monitoring apparatus detects the user's breath, and thereafter the controller controls the operation of the motor fan synchronously with the user's breath based on the detection signal sent from the breath monitoring apparatus, and the controller stops the motor fan when the breath monitoring apparatus does not detect the user's breath for a predetermined time.

2. A breathing apparatus of claim 1, further comprising:
   (g) an alarm, and wherein the breath monitoring apparatus is an apparatus for monitoring an internal pressure of the face piece, and the controller starts the alarm when the apparatus for monitoring the internal pressure of the face piece detects negative pressure.

3. A breathing apparatus of claim 1, wherein the circular disk portion is flat to abut an end of the first portion of the annular drum projecting out of the face piece at a radial middle when internal pressure of the face piece balances with the external pressure of the face piece, and the magnet is provided on a center of the circular disk portion.

4. A breathing apparatus of claim 3, wherein the inner periphery of the annular portion includes a thick portion that is fixed to a circumferential groove formed on the outside surface of the first portion of the annular drum.

5. A breathing apparatus of claim 3, further comprising:
   (h) a cover provided on an outside surface of the face piece, wherein the cover is disposed to cover the breath monitoring apparatus, and the cover includes an air hole communicating with an external environment.

6. A breathing apparatus of claim 5, wherein the annular drum includes a partition disposed at a longitudinal middle position within the annular drum, wherein the partition includes a plurality of holes formed at an outer periphery of the partition and circumferentially distanced from each other.

7. A breathing apparatus of claim 6, wherein the inhale valve is a reed valve and the exhale valve is a reed valve.

* * * * *